(12) United States Patent
Canfield (10) Patent No.: US 8,696,572 B2
(45) Date of Patent: Apr. 15, 2014

(54) MEDICAL SYSTEM WITH COMPREHENSIVE REPORT SIMULATION FEATURE

(75) Inventor: Earl Canfield, Snohomish, WA (US)

(73) Assignee: Koninklijke Philips N.V., Eindhoven (NL)

( * ) Notice: Subject to any disclaimer, the term of this patent is extended or adjusted under 35 U.S.C. 154(b) by 740 days.

(21) Appl. No.: 12/439,848

(22) PCT Filed: Sep. 4, 2007

(86) PCT No.: PCT/IB2007/053559
§ 371 (c)(1),
(2), (4) Date: Mar. 4, 2009

(87) PCT Pub. No.: WO2008/032239
PCT Pub. Date: Mar. 20, 2008

(65) Prior Publication Data
US 2009/0326898 A1    Dec. 31, 2009

Related U.S. Application Data

(60) Provisional application No. 60/825,223, filed on Sep. 11, 2006.

(51) Int. Cl.
*A61B 8/00* (2006.01)

(52) U.S. Cl.
USPC ........... 600/437; 600/439; 600/443; 600/447; 600/407

(58) Field of Classification Search
USPC ......................... 600/437, 439, 443, 447, 407
See application file for complete search history.

(56) References Cited

U.S. PATENT DOCUMENTS

| 6,306,089 B1 * | 10/2001 | Coleman et al. ............... 600/437 |
| 8,235,726 B2 * | 8/2012 | Hostettler et al. ............ 434/262 |
| 2005/0054927 A1 | 3/2005 | Love |

\* cited by examiner

*Primary Examiner* — Joel Lamprecht (57) ABSTRACT

A medical system includes a display for displaying an image and an analysis package operatively connected to the image display. The analysis package provides a user the ability to create a comprehensive report of all system functionality using simulated input from an exhaustive database of system input device values and user input values.

18 Claims, 7 Drawing Sheets

| Patient Report | | | | |
|---|---|---|---|---|
| LNAME, FNAME | PAT ID | 56y | M 6'1" 190lb | 03/29/2006 Test Hospital |

LNAME, FNAME
Patient ID: PAT ID
Study Date: 03/29/2006    Accession #: TEST
Institution Name: Test Hospital
Ref. M.D.: MD    Sonographer: MMM
DOB: 01/01/1950    Age: 56y    Ht: 6'1"    Wt: 190lb    Gender: M
Comments: TEST COMMENTS

Adult Echo

Adult Echo - Patient Study Info and Comments
Height    6'1"    Weight    190lb    BSA    2.11 m²
Sys / Dias BP: 120/70    MAP 87
☑ Smoker    ☑ Hypertension    ☑ Pacemaker
☑ Hx of Rheumatic Fever    ☑ Congestive Heart Failure
Surgeries:    TEST SURGERIES
   Indications:    Type    S    Grade    1    Valve Replacement
☑ Murmur    AV Block        Bioprosthetic
☑ Arrhythmia    ☑ Jugular Venous Distension    Type    TEST
☑ Chest Pain    ☑ Peripheral Edema    Date    01/01/2001
☑ Dyspnea    ☑ Ascites
☑ Fatigue    ☑ Infection    Mechanical
☑ Syncope    ☑ Fever of Unknown Origin    Type    TEST
☑ Dizziness    ☑ TIA/Stroke    Date    01/01/2001
☑ Hemoptysis LNAME, FNAME    03/29/2006    Page 1 of 51

[Short Report] [Long Report] [Edit Report] [Findings] [Configure] [Close]

| Patient Report | | | | | | | |
|---|---|---|---|---|---|---|---|
| LNAME, FNAME | | PAT ID | 56y | | M 6'1" | 190lb | 03/29/2006 Test Hospital |
| Vessels | | | | | | | |
| AoR Diam (2D) | Avg | 1 | 2 | 3 | 4 | 5 | |
| Dist | 0.3 cm | 0.1 | 0.2 | 0.3 | 0.4 | 0.5 | |
| Asc Ao Diam | Avg | | | | | | |
| Dist | 0.3 cm | 0.1 | 0.2 | 0.3 | 0.4 | 0.5 | |
| Desc Ao Diam | Avg | | | | | | |
| Dist | 0.3 cm | 0.1 | 0.2 | 0.3 | 0.4 | 0.5 | |
| MPA Diam | Avg | | | | | | |
| Dist | 0.3 cm | 0.1 | 0.2 | 0.3 | 0.4 | 0.5 | |
| RVOT Diam | Avg | | | | | | |
| Dist | 0.3 cm | 0.1 | 0.2 | 0.3 | 0.4 | 0.5 | |

LNAME, FNAME  03/29/2006  Page 6 of 51

Short Report | Long Report | Edit Report | Findings | Configure | Close

FIGURE 4c

Patient Report

LNAME, FNAME          PAT ID          56y          M 6'1"          190lb          03/29/2006  Test Hospital Tricuspid Valve

| | | 1 | 2 | 3 | 4 | 5 |
|---|---|---|---|---|---|---|
| TV D-E Exc | Avg | | | | | |
| Dist | 0.3 cm | 0.1 | 0.2 | 0.3 | 0.4 | 0.5 |
| TV D-E Slope | Avg | | | | | |
| Slope | 0.3 cm/s | 0.1 | 0.2 | 0.3 | 0.4 | 0.5 |
| TV E-F Slope | Avg | | | | | |
| Slope | 0.3 cm/s | 0.1 | 0.2 | 0.3 | 0.4 | 0.5 |
| TV A-C Interval | Avg | | | | | |
| Time | 3 ms | 1 | 2 | 3 | 4 | 5 |

Pulmonic Valve

RV PEP/ET     1.00

LNAME, FNAME          03/29/2006          Page 21 of 51

Short Report | Long Report | Edit Report | Findings | Configure | Close

FIGURE 4d

Patient Report

| LNAME, FNAME | PAT ID | 56y | M 61" | 190lb | 03/29/2006 Test Hospital |

Findings
LV Size/Shape
  The left ventricle is not well visualized
  A basal posterior aneurysm is present
  A basal lateral aneurysm is present
  The left ventricle is grossly normal size
  The left ventricle is normal in size
  The left ventricular cavity is small
  LV is severely dilated
  There is no left ventricular aneurysm
  Apical aneurysm, large
  A pseudoaneurysm is present
  A basal inferior aneurysm is present
TV Structure
  The tricuspid valve is not well visualized Page 50 of 51

LNAME, FNAME        03/29/2006

Findings (cont.)
  The non-septal leaflet is thickened
  Apical leaflet displacement raises possibility of Ebstein's anomaly
  Valvular appearance consistent with carcinoid heart disease
  There is no tricuspid annular calcification
  There is tricuspid annular calcification iSCAN

- Short Report
- Long Report
- Edit Report
- Findings
- Configure
- Close

MEDICAL SYSTEM WITH COMPREHENSIVE REPORT SIMULATION FEATURE

This invention relates to medical systems and, more particularly, to medical diagnostic ultrasound systems that automatically generate a comprehensive simulated report of the system's capabilities for demonstration and validation purposes.

Although the background and embodiments of the invention are described below in the context of an ultrasound imaging system, it will be understood that the invention may be practiced on other types of medical systems. In the past, general purpose ultrasound imaging systems were used to provide images of all anatomical features that could be imaged using ultrasound. But as ultrasound diagnosis has become more sophisticated and the technology more refined, ultrasound imaging systems have become more specialized and configured for imaging specific anatomy during certain specific types of examinations such as obstetrics, cardiology, vascular and radiology. In the recent past the practice of ultrasound diagnosis has become more standardized, with specific image acquisition protocols being designed for patients with specific symptoms or characteristics. For example, a general abdominal exam protocol may call for the acquisition of particular views of the liver, kidneys, gall bladder and pancreas. A general vascular exam may call for the acquisition of particular views of the carotid artery and vasculature of the limbs of the body. As ultrasound imaging systems have evolved to provide for such protocols, the complexity of the system has increased considerably. As a result, a typical ultrasound imaging system is capable of generating a great number of measurements, calculations and reports. Doctors, clinicians and sonographers typically use ultrasound imaging systems to do measurements. Typical measurements might include estimates of gestational age of a fetus or measurements of the heart wall or blood vessel thickness. Ultrasound imaging systems are capable of making reports for every type of examination and each type of report can be different since each type of exam can include different measurements. It is therefore possible to create many different reports and measurements with a typical ultrasound imaging system. Other types of medical systems are similarly sophisticated.

Due to the large number of possible exams, measurements and reports, very few people have the time or ability to generate a comprehensive report with all images, measurements and calculations. To do so requires applying a large amount of data to the medical system and can produce a very lengthy report containing a great deal of extraneous information for the diagnosing or referring physician. Obviously, this takes a great deal of time. Yet every time a new version of the system is released, the capabilities of the system must be tested and validated with many external vendors and hospitals who use or work with the ultrasound system. Such prior art systems force system engineers and vendors to manually enter data to validate the operation of the system and its data parsing algorithms. Because of this limitation, comprehensive testing is very difficult or impossible. Likewise, a sales representative giving a field demonstration is capable of demonstrating only a limited and pre-computed subset of the functions, calculations and reports of any such prior art system. Because of these limitations, end users, vendors, maintenance personnel, clinical specialists, in-house testers and sales representatives are forced to test and demonstrate the system in an inefficient manner.

There is therefore a need for a medical system that allows all users to create simulated reports of the system's capabilities in a manner that is both complete and efficient.

This invention is directed to a medical system that automatically generates a comprehensive simulated report of the system's capabilities for demonstration and validation purposes. As discussed above, applying a large amount of data to, for example, an ultrasound imaging system is quite laborious due to the large number of different exams, measurements and calculations that are possible with such systems. In one embodiment of the invention, a store of data is created and it is this data that is applied to the medical system for generating reports. The data is typically stored in one or more databases. For example, patient data and analysis calculations may be stored in one or more databases and reports are generated from the data dictionaries of such databases. The number and type of reports is limited only by the amount of data stored in the database or databases. Patient data is the raw data that would be typically gathered by the medical system and from the user of the system. In an ultrasound imaging system, for example, this raw data could include the data stream of the transducer which is used by the system to create images of the internal organs. Analysis calculations are analytical results of the exam, and might include, for example, the sizes or performance parameters of various internal organs. Data and analysis calculations can be stored for every type of exam, calculation and report. Such data is then used as input to the system through all possible sets of exams and calculations and thus creates a complete and comprehensive report. It will be understood that the invention is not a store of pre-compiled or "canned" reports. Rather, it is a store of data which can be played back to the medical system in order to simulate an actual exam and the generation of an actual report. The medical system itself is not aware that the data and other input is coming from anywhere other than normal input devices, such as a transducer and user. The reports generated in this fashion are not only comprehensive, but force the system to function as it would during a real exam.

Figure 1:
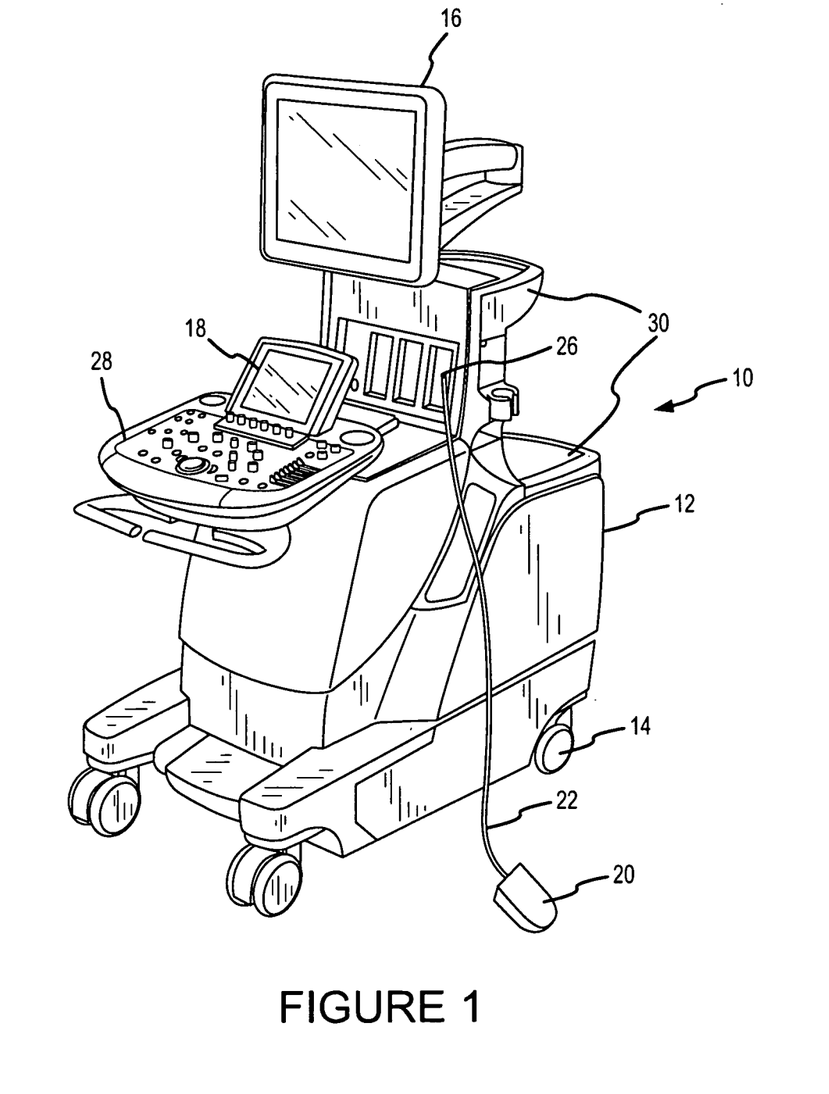
FIG. 1 is an isometric view of a diagnostic ultrasound system according to one example of the invention.

A medical system 10 according to one example of the invention is illustrated FIG. 1. This example medical system, an ultrasound imaging system, is used for illustrative purposes only and other types of medical systems may also be used. The system 10 includes a chassis 12 containing most of the electronic circuitry for the system 10. The chassis 12 is mounted on a cart 14, and a display 16 is mounted on the chassis 12. An imaging probe 20 is connected through a cable 22 to one of three connectors 26 on the chassis 12. The chassis 12 includes a keyboard and controls, generally indicated by reference numeral 28, for allowing a sonographer to operate the medical system 10 and enter information about the patient or the type of examination that is being conducted. At the back of the control panel 28 is a touchscreen display 18 on which programmable softkeys are displayed for supplementing the keyboard and controls 28 in controlling the operation of the system 10.

In operation, the imaging probe 20 is placed against the skin of a patient (not shown) and held stationary to acquire an image of blood or tissues in a volumetric region beneath the skin. The volumetric image is presented on the display 16, and it may be recorded by a recorder (not shown) placed on one of the two accessory shelves 30. The system 10 may also record or print a report containing text and images. Data corresponding to the image may also be downloaded through a suitable data link, such as the Internet or a local area network. In addition to using the two-dimensional probe 20 to shown a volumetric image on the display, the ultrasound imaging system may also provide other types of images using the probe 20, and it may accept other types of probes (not shown) to provide other types of images.

Figure 2:
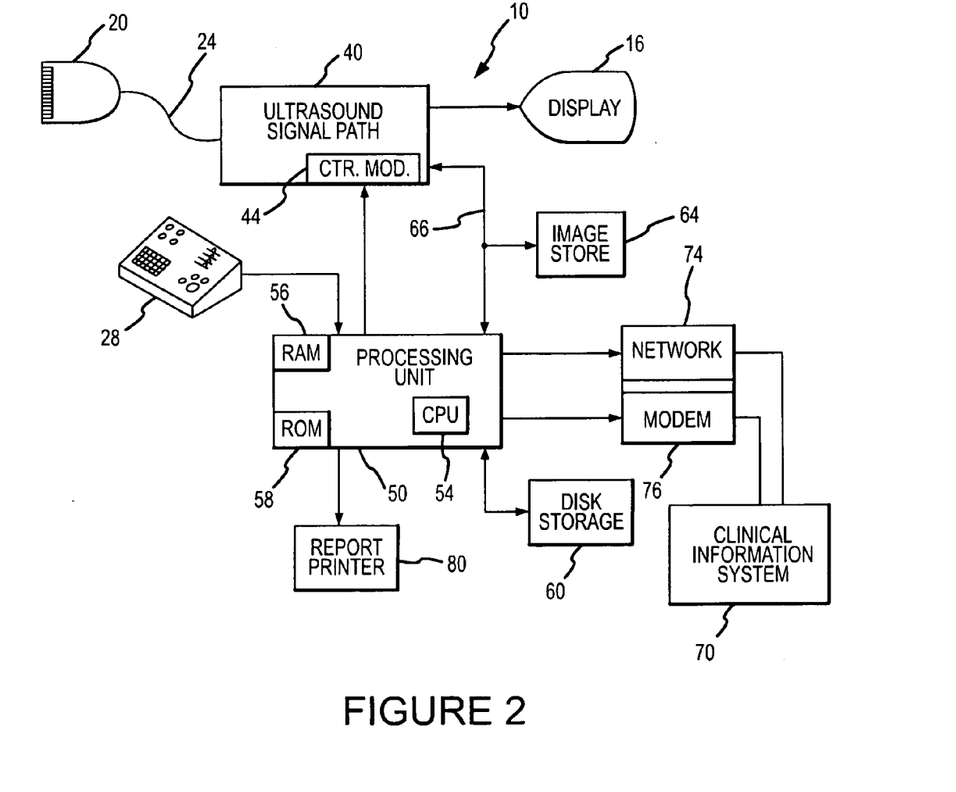
FIG. 2 is a block diagram of the components used in the ultrasound system of FIG. 1.

The electrical components of the medical system 10 are illustrated in FIG. 2. As mentioned above, the ultrasound imaging probe 20 is coupled by the cable 22 to one of the connectors 26, which are connected to an ultrasound signal path 40 of conventional design. As is well-known in the art, the ultrasound signal path 40 includes a transmitter (not shown) coupling electrical signals to the probe 20, an acquisition unit (not shown) that receives electrical signals from the probe 20 corresponding to ultrasound echoes, a signal processing unit (not shown) that processes the signals from the acquisition unit to perform a variety of functions such as processing returns from specific depths or processing returns from blood flowing through vessels, and a scan converter (not shown) that converts the signals from the signal processing unit so that they are suitable for presentation of an image or display by the display 16. The processing unit in this example is capable of processing both B mode (structural) and Doppler (flow or motion) signals for the production of various B mode and Doppler volumetric images, including spectral Doppler volumetric images. The ultrasound signal path 40 also includes a control module 44 that interfaces with a processing unit 50 to control the operation of the ultrasound signal path. The ultrasound signal path 40 may, of course, contain components in addition to those described above and, in suitable instances, some of the components described above may be omitted.

The processing unit 50 contains a number of components, including a central processor unit ("CPU") 54, random access memory ("RAM") 56, and read only memory ("ROM") 58, to name a few. As is well-known in the art, the ROM 58 stores a program of instructions that is executed by the CPU 54, as well as initialization data for use by the CPU 54. The RAM 56 provides temporary storage of data and instructions for use by the CPU 54. The processing unit 50 interfaces with a mass storage device such as a disk drive 60 for permanent storage of data, such as data corresponding to ultrasound images obtained by the system 10. The image data is initially stored in an image storage device 64 referred to as a Cineloop® memory that is coupled to a signal path 66 extending between the ultrasound signal path 40 and the processing unit 50 to provide temporary storage of received images. The disk drive 60 also preferably stores protocols which may be called up and initiated to guide the sonographer through various ultrasound exams.

The processing unit 50 also interfaces with the keyboard and controls 28. The keyboard and controls 28 may be manipulated by the sonographer to cause the medical system 10 to produce automatically generated reports at the conclusion of an examination. The processing unit 50 preferably interfaces with a report printer 80 that prints reports containing text and one or more images. The type of reports provided by the printer 80 depends on the type of ultrasound examination that was conducted by the execution of a specific protocol. Finally, as mentioned above, data corresponding to the image may be downloaded through a suitable data link, such as a network 74 or a modem 76, to a clinical information system 70 or other device.

A comprehensive report is of great value to a number of different users of such a medical system. In addition to physicians, medical system testers and maintenance personnel, vendors and field sales representatives are but three other types of users for whom such reports are of value.

Typically, embodiments of the present invention will benefit medical system testing the most. Prior to releasing a medical system for sale and use by the public, a medical system manufacturer needs to test the system to insure data accuracy and integrity. Such tests might include stress tests, image capture verification, including tests of scale and color saturation, as well as basic user interface tests. One embodiment of the invention allows testers to accomplish all these types of tests by storing the instrument and user input for later re-play and simulation. A comprehensive report of all system functionality of, for example, an ultrasound imaging system will typically comprise several hundred pages. Generating such a report is in itself a stress test of the system. Likewise, maintenance personnel must re-verify the integrity of a medical system after making a repair to the system. The ability to quickly generate a comprehensive report of all system functionality allows maintenance personnel to quickly and effectively put medical systems back in service.

Medical system vendors also benefit from the ability to simulate reports. A vendor, in this context, is a reseller of medical systems. Typically, a vendor will purchase such a system, add value to the system in some fashion, and then re-sell the augmented system to hospitals and clinics. A vendor might, for example, add value to an ultrasound imaging system by creating custom data parsing algorithms or custom examination protocols. Vendors preferably want data samples which contain all possible data items to validate their data parsing algorithms. One embodiment of the invention allows vendors to accomplish such validation quickly and accurately.

While a field sales representative may also benefit from a comprehensive report, such a report would be too large for use as a sales tool. One embodiment of the invention allows a field sales representative to simulate only a subset of the full medical system functionality. Although the report is no longer comprehensive, creating such a report is accomplished through simulating the medical system functionality of interest to the particular the customer. Such report generation is preferable to pre-computed, "canned"reports because they are created by simulating an actual exam and the demonstration of the medical system uses realistic measurements which are medically valid. The sample report is of the type of information which is used by the customer, making it relevant to his or her medical practice.

Figure 3:
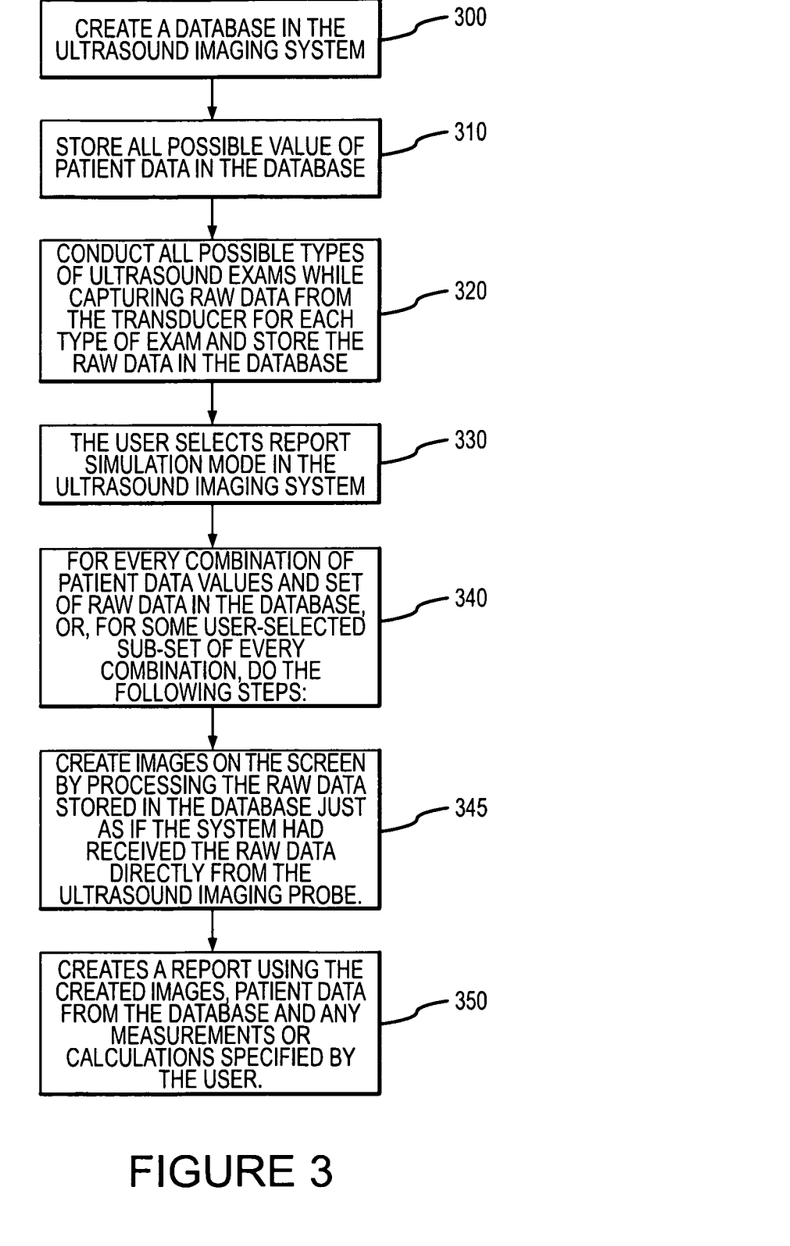
FIG. 3 is a flowchart of an embodiment of the present invention implemented on an ultrasound imaging system.

A flowchart of an embodiment of the invention as implemented in a medical ultrasound imaging system is illustrated in FIG. 3. At step 300, a database is created within the ultrasound imaging system. This database is used to store a comprehensive collection of possible patient data at 310. Patient data includes such things as patient name, age, sex, prior medical history, and the like. The database is used to store a collection of raw data at 320. This raw data would typically be that which is carried by the ultrasound signal path 40 as described above. The raw data could, however, be some intermediate form of data. For example, the raw data could come from each of the elements of the transducer in the ultrasound imaging probe 20, or the raw data could be that of the beam former (not shown) prior to scan conversion of the beam-formed data into an image format. No matter the form of the raw data, embodiments of the invention will perform substantial processing of the data in order to render ultrasound images just as it would do if the data was being created in real-time during an actual examination. In this manner, the ultrasound imaging system is forced to behave as if an actual exam was taking place and preferably allowing the user to interact with the system just as a sonographer would do during an actual exam.

Once the patient data and raw data for each type of exam has been stored in the database, the system is ready to create a simulated report by entering the report simulation mode at 330. After entering report simulation mode, the usual behavior of this embodiment is to simulate a report based on every combination of patient data and raw data in the database at 340, 345 and 350. This would create the most comprehensive report possible and would be of the greatest value to testers or maintenance personnel. Alternatively, the user may select a sub-set of the available patient data and raw data at 340. In a typical demonstration scenario, a field sales representative does not have the time to demonstrate, nor does the typical customer have an interest in viewing, every possible bit of system functionality. By permitting a sub-set of the data to be selected, the field sales representative can demonstrate only the types of exams that are of interest to the customer. For instance, the representative could choose to demonstrate a vascular exam with vascular data or a cardiac exam with cardiac data to a cardiologist. Because the system remains interactive, the field sales representative can demonstrate the abilities of the system as if an actual exam were taking place.

Figure 4A:
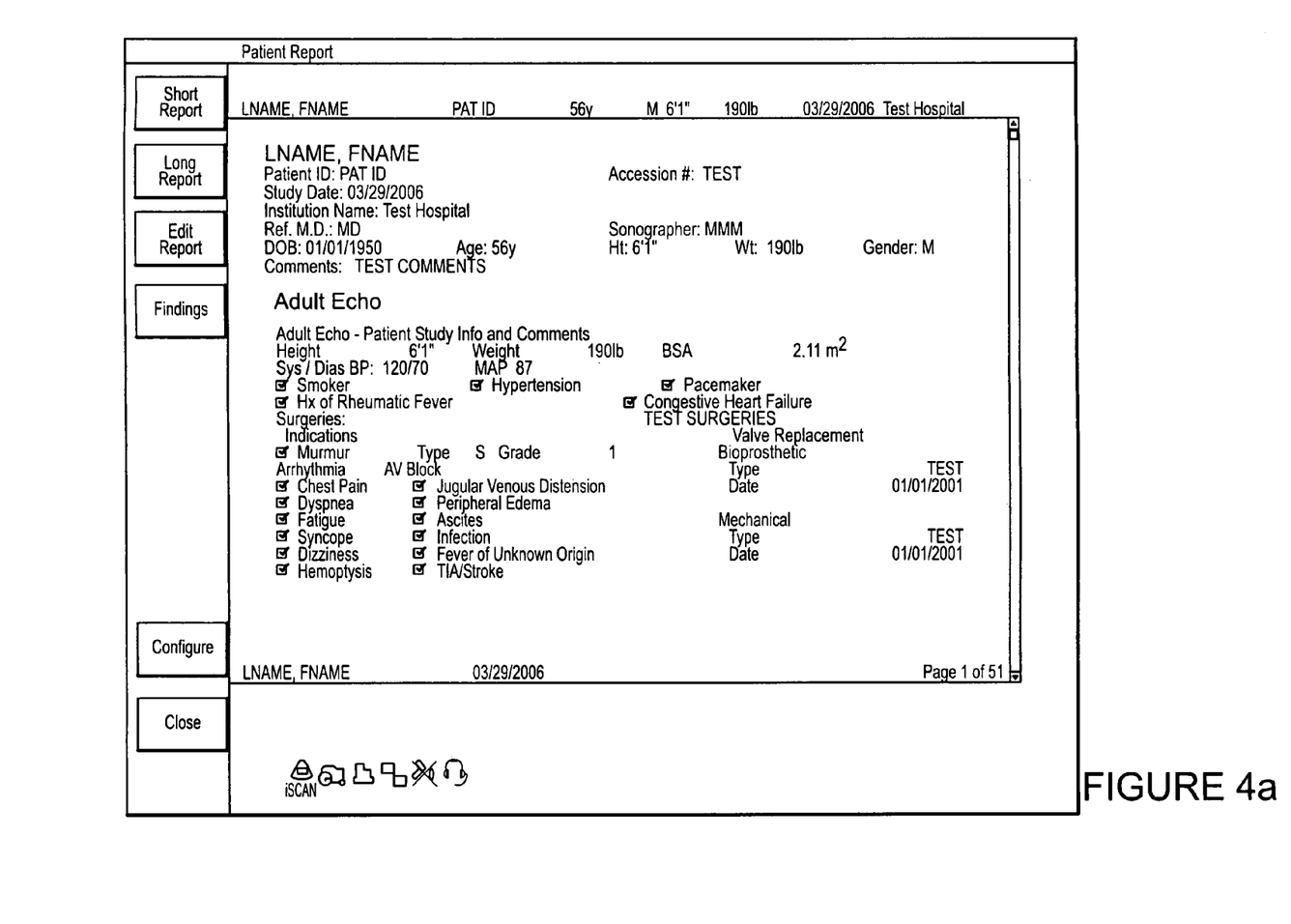
FIGS. 4a-4d illustrate examples of report simulator output.
Figure 4B:
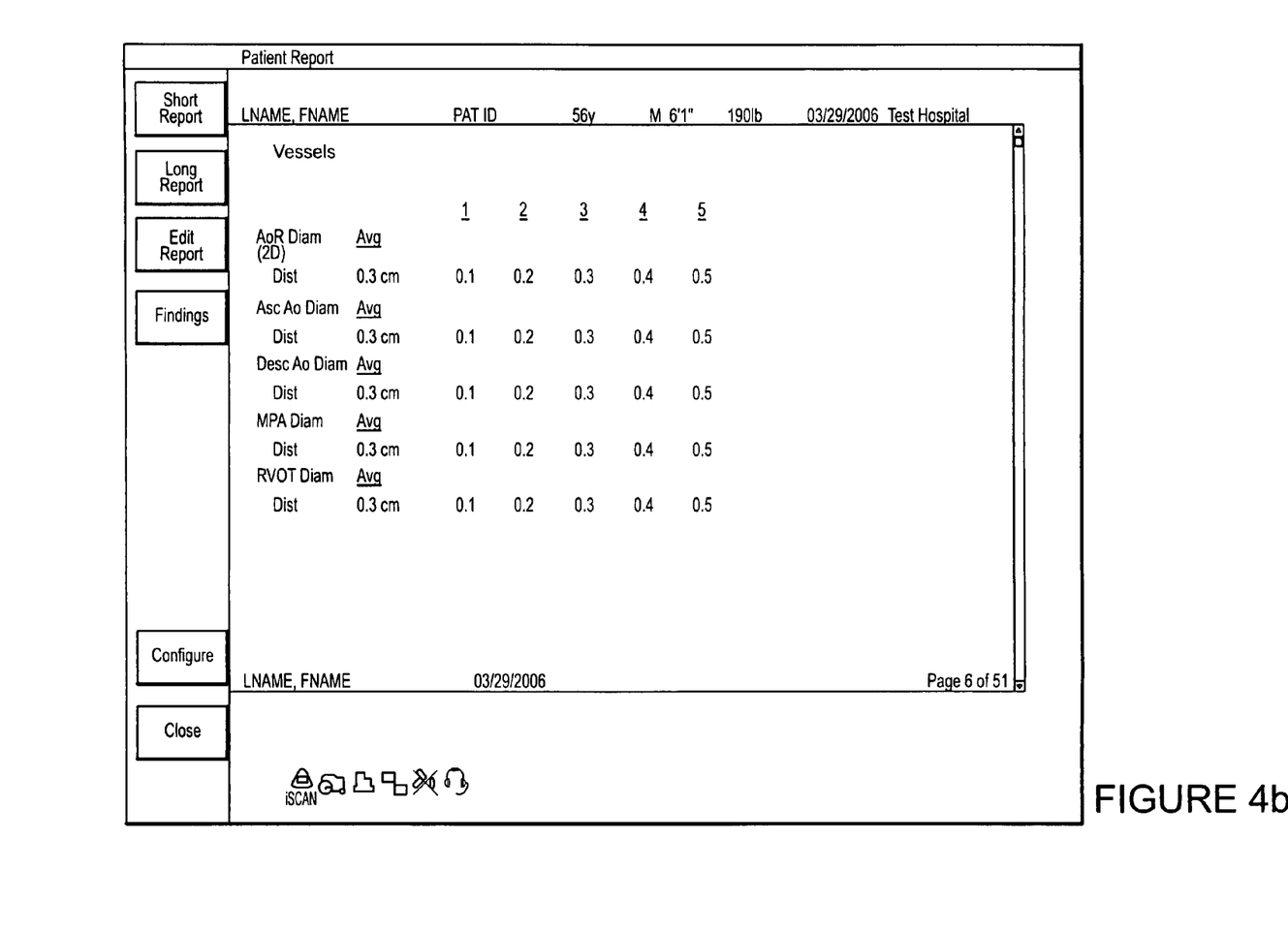
Figure 4C:
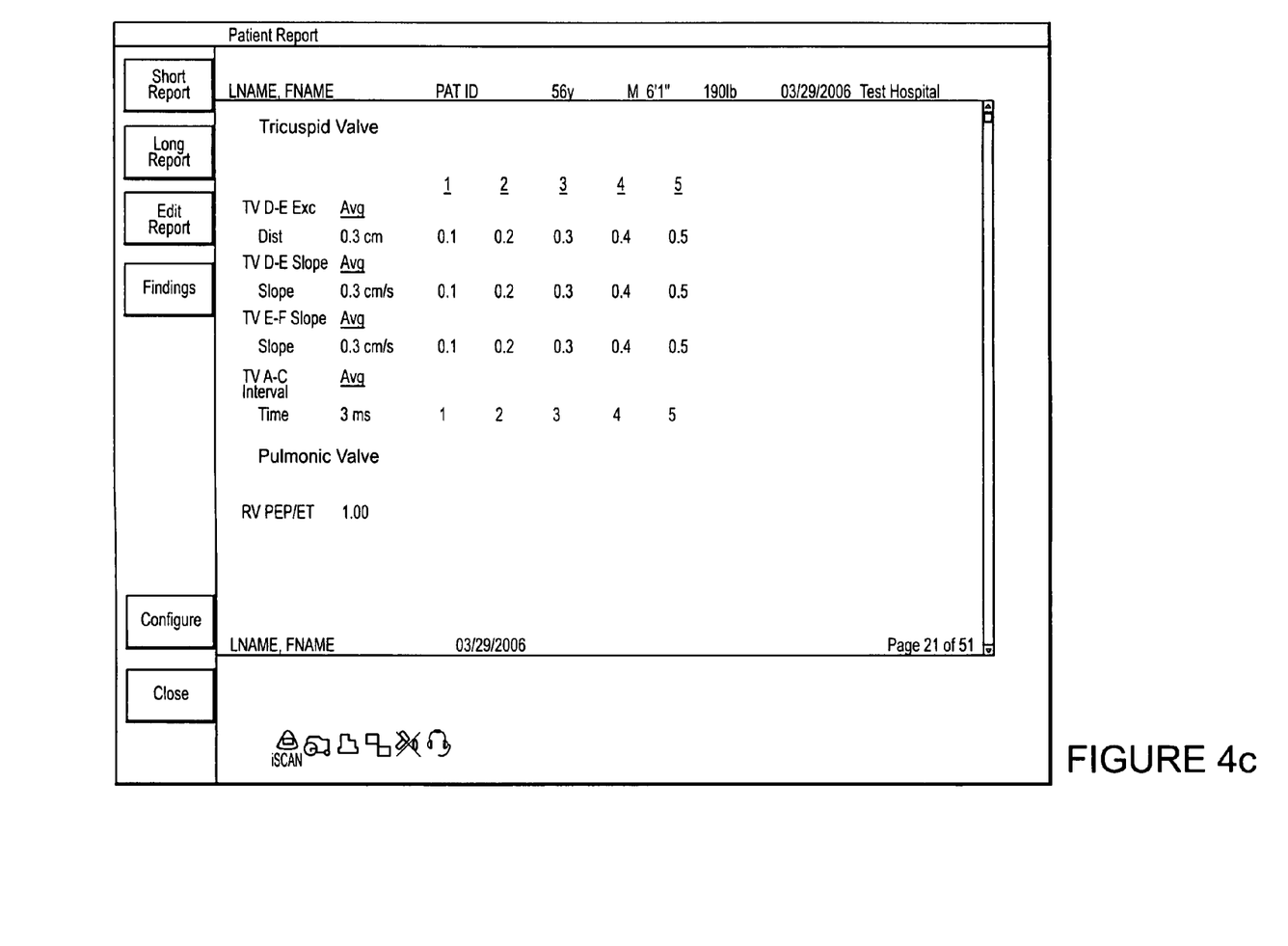
Figure 4D:
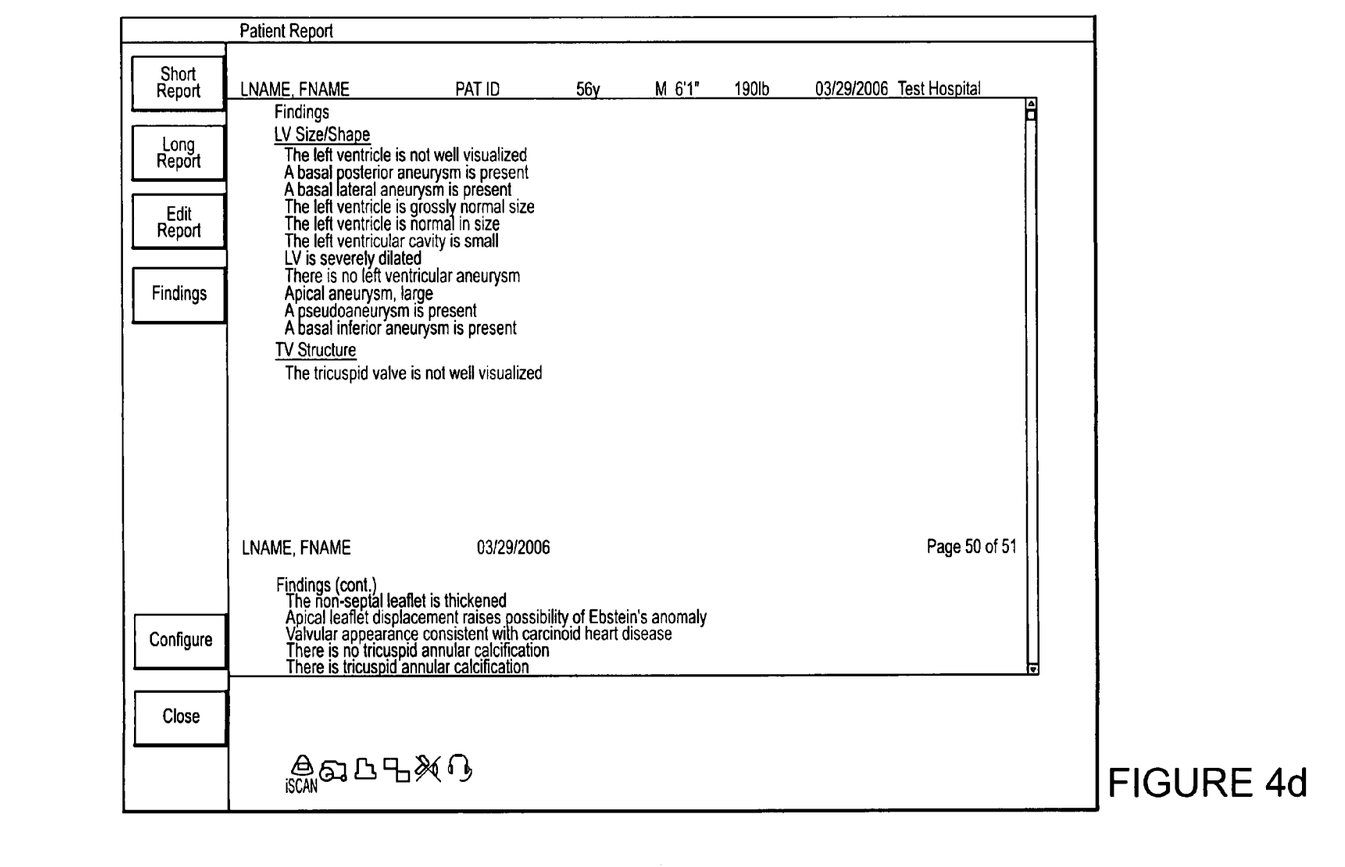

FIGS. 4a-4d illustrate several pages of simulated report. This simulated report is based on but a single cardiac examination and nevertheless, in a particular constructed embodiment, comprises fifty-one pages. FIG. 4a illustrates the first page of the simulated report. This page contains basic patient information and diagnostic information. FIG. 4b illustrates the simulated report output of heart vessel measurements. FIG. 4c illustrates the simulated report output of measurements of the tricuspid valve. Finally, FIG. 4d illustrates the final medical findings about the left ventricle.

Although the present invention has been described with reference to the disclosed examples, persons skilled in the art will recognize that changes may be made in form and detail without departing from the spirit and scope of the invention. Such modifications are well within the skill of those ordinarily skilled in the art. Accordingly, the invention is not limited except as by the appended claims.

What is claimed is:

1. In a medical ultrasound system, a method for creating a comprehensive report simulation, the method comprising:
   storing patient data which is not image data and raw data simulating signals representative of data produced by a plurality of different types of ultrasound exams and analysis calculations for reports to be produced by the medical system in a first database contained in the medical system, the raw data simulating actual data produced by the medical system for a comprehensive exam report;
   processing the raw data to obtain data corresponding to ultrasound images suitable for presentation in an exam report; and
   using the patient data and the ultrasound images to create a report simulation.

2. The method of claim 1 wherein storing patient data in the first database comprises storing patient information regarding a plurality of patients.

3. The method of claim 1 wherein the raw data of an ultrasound transducer simulates that obtained from an ultrasound transducer when used to image anatomy.

4. The method of claim 1 wherein creating a report simulation comprises creating a report based on raw data simulating actual input to the medical ultrasound system, the simulated input being provided by the patient data and processed raw data, instead of input from input devices and users during an actual patient exam.

5. The method of claim 4 wherein the patient data comprises patient information regarding a plurality of patients and the processed raw data comprises raw data that corresponds to the signals associated with a plurality of types of exams, and further wherein using the patient data and processed raw data to create a report simulation comprises using different combinations of patient data and processed raw data from the first database to simulate a report.

6. The method of claim 4 wherein the patient data comprises patient information regarding a plurality of patients and the processed raw data comprises raw data that corresponds to the signals associated with a plurality of types of exam, and further wherein using the patient data and processed raw data to create a report simulation comprises using a user selected subset of different combinations of patient data and processed raw data from the first database to simulate a report.

7. The method of claim 1 wherein the medical system remains responsive to user interaction during using the patient data and the ultrasound images to create a report simulation.

8. A medical ultrasound system comprising:
   a display; a processor coupled to the display; a user interface coupled to the processor; and
   an analysis package stored on a computer readable medium and operatively connected to the processor, the analysis package providing a user the ability to create a comprehensive report simulation, the analysis package being configured to:
   store patient data which is not image data and raw data simulating signals representative of an an actual input device data stream that would be produced by the ultrasound system during a plurality of exam types in a first database contained in the medical system;
   process the raw data simulating signals representative of an input device data stream to obtain data corresponding to ultrasound images suitable for presentation in an exam report; and
   use the patient data and the ultrasound images to create a report simulation.

9. The medical ultrasound system of claim 8 wherein the analysis package is further configured to store patient information regarding a plurality of patients in the first database.

10. The medical ultrasound system of claim 8 wherein the analysis package is further configured to store raw data simulating the signals associated with a plurality of types of exam.

11. The medical ultrasound system of claim 8 wherein the analysis package is further configured to create a report based on simulated input to the medical system, the simulated input being provided by the patient data and processed raw data, instead of input from input devices and users during an actual patient exam.

12. The medical ultrasound system of claim 11 wherein the patient data comprises patient information regarding a plurality of patients and the processed raw data comprises raw data that corresponds to the signals associated with a plurality of types of exam, and further wherein the analysis package is configured to use the patient data and processed raw data to create a report simulation using different combinations of patient data and processed raw data from the first database.

13. The medical ultrasound system of claim 11 wherein the patient data comprises patient information regarding a plurality of patients and the processed raw data comprises raw data that corresponds to the signals associated with a plurality of types of exam, and further wherein the analysis package is further configured to use the patient data and processed raw data to create a report simulation by using a user selected subset of different combinations of patient data and processed raw data from the first database.

14. The medical ultrasound system of claim 8 wherein the analysis package comprises hardware and software which is responsive to image data produced by the medical ultrasound system.

15. The medical ultrasound system of claim 14 wherein the analysis package can be configured for a particular type of diagnostic application.

16. The medical ultrasound system of claim 15 wherein the particular type of diagnostic application comprises one of OB, GYN, general imaging, vascular, or cardiology.

17. The medical ultrasound system of claim 16 wherein the particular type of diagnostic application comprises OB, and further comprising an exam protocol which is a fetal exam protocol.

18. The medical ultrasound system of claim 8 wherein the analysis package is further configured to allow the medical ultrasound system to remain responsive to user interaction during the creation of the report simulation.

\* \* \* \* \*